United States Patent
Tazawa et al.

(10) Patent No.: US 8,329,454 B2
(45) Date of Patent: Dec. 11, 2012

(54) DEVICE FOR DETECTING A CHOLINESTERASE-INHIBITING SUBSTANCE COMPRISING A HYDROPHILIC PHOTO-CROSSLINKABLE RESIN

(75) Inventors: Hidekatsu Tazawa, Kanagawa (JP); Tomohiko Ebata, Kanagawa (JP); Takahide Takadera, Kanagawa (JP); Naonori Miyata, Kanagawa (JP)

(73) Assignees: Institute of Microchemical Technology Co., Ltd., Kanagawa (JP); Kansai Paint Co., Ltd., Hyogo (JP)

( * ) Notice: Subject to any disclaimer, the term of this patent is extended or adjusted under 35 U.S.C. 154(b) by 0 days.

(21) Appl. No.: 12/989,152

(22) PCT Filed: Apr. 23, 2009

(86) PCT No.: PCT/JP2009/058105
§ 371 (c)(1),
(2), (4) Date: Jan. 21, 2011

(87) PCT Pub. No.: WO2009/131194
PCT Pub. Date: Oct. 29, 2009

(65) Prior Publication Data
US 2011/0124023 A1    May 26, 2011

(30) Foreign Application Priority Data
Apr. 24, 2008  (JP) ................. 2008-114556

(51) Int. Cl.
*C12M 1/00* (2006.01)
(52) U.S. Cl. ............................ 435/287.9
(58) Field of Classification Search .......... 435/20, 435/287.7, 287.9
See application file for complete search history.

(56) References Cited

U.S. PATENT DOCUMENTS

| | | | | |
|---|---|---|---|---|
| 4,324,858 A | * | 4/1982 | Goodson et al. | ............ 435/20 |
| 2010/0041077 A1 | * | 2/2010 | Nagy et al. | ............ 435/7.92 |

FOREIGN PATENT DOCUMENTS

| | | |
|---|---|---|
| JP | 1-157386 | 6/1989 |
| JP | 2002-543396 | 12/2002 |
| JP | 2003-4720 | 1/2003 |
| WO | 00/65081 | 11/2000 |
| WO | WO 00/65081 | * 11/2000 |

OTHER PUBLICATIONS

International Search Report issued Jul. 28, 2009 in International (PCT) Application No. PCT/JP2009/058105.
Masashi Ugaki et al., "Electrophoretic Analysis of Nonspecific Esterases and Acetylcholinesterases from the Housefly, *Musca domestica* L. (Diptera: Muscidae), with Reference to Organophosphorous Insecticide Resistance", Appl. Ent. Zool., 1983, vol. 18, No. 4, pp. 447-455.
Hidekatsu Tazawa et al., "Noyaku Kan'i Kensa Kit 'Agurikemu' no Kaihatsu", Tokyo Konfarensu 2008 Koen Yoshishu, The Japan Society for Analytical Chemistry, Sep. 3, 2008, p. 65.
Hidekatsu Tazawa et al., "Noyaku Kan'i Kensa Kit 'Agurikemu TM' no Kaihatsu ", Dai 31 Kai Pesticide Residue Analysis Committee Koen Yoshishu, Nov. 25, 2008, pp. 250-257.
Hidekatsu Tazawa et al., "Zamyu Noyaku no Taseibun Ko Kando Screening-ho ni Tsuite Zanryu Noyaku Kensa Kit-Agurikemu TM-", Food and Packaging, Sep. 1, 2008, pp. 543-546.

* cited by examiner

*Primary Examiner* — Ralph Gitomer
(74) *Attorney, Agent, or Firm* — Wenderoth, Lind & Ponack, L.L.P.

(57) ABSTRACT

A device for detecting a cholinesterase-inhibiting substance comprising a basal layer fixed at the bottom of a container, and a cholinesterase-containing reaction layer which is fixed on the basal layer, wherein the basal layer and the cholinesterase-containing reaction layer comprises a hydrophilic photo-crosslinkable resin.

3 Claims, 3 Drawing Sheets

(a)

(b)

DEVICE FOR DETECTING A CHOLINESTERASE-INHIBITING SUBSTANCE COMPRISING A HYDROPHILIC PHOTO-CROSSLINKABLE RESIN

This application is a National Stage application filed under Rule 371 based on PCT/JP2009/058105 filed Apr. 23, 2009.

TECHNICAL FIELD

The present invention relates to a device, a kit and a method for detection of a cholinesterase-inhibiting substance.

ORIGINAL SUMMARY OF THE INVENTION

A detection device comprises a basal layer fixed at the bottom of a container therein, and a cholinesterase-containing reaction layer is fixed on the basal layer. A sample is added to the detection device, and the presence of a cholinesterase-inhibiting substance in the sample is visually determined through coloring reaction. For detecting an organophosphate agrichemical, the sample is brought into contact with an oxidizing agent on a column to convert it into the oxon form thereof.

BACKGROUND ART

Heretofore, it is known that agrichemical ingredients remaining in agricultural crops, drinkable water and the like have some negative influences on human bodies.

In particular, organophosphate agrichemicals and carbamate agrichemicals containing a cholinesterase-inhibiting substance involve serious problems as causing nervous disorders.

Given that situation, for supplying secure foods, drinkable water and the like, it is desired to develop the technology for detection of residual agrichemicals, and up to now, various devices and methods for detection of agrichemicals have been proposed.

Many of agrichemical detection methods heretofore employed use analytical instrumentation of gas chromatography (GC), gas chromatographic mass spectrometry (GC/MS), liquid chromatography (LC), liquid chromatographic mass spectrometry (LC/MS) or the like.

Such analytical methods have the advantage of the possibility of high-sensitivity identification and quantitative determination, but are, on the other hand, disadvantageous in that they require large-scale equipments and complicated operations and take a lot of time for inspection, and therefore could not attain multi-sample analysis and on-site inspection.

As in the above, instrumental analysis requires time and effort. Therefore, Patent Reference 1 discloses a method for detection of organophosphate agrichemicals and carbamate agrichemicals by measuring the level of substrate degradation by hydrolysis, based on the action of the cholinesterase-inhibiting substance in the agrichemicals to inactivate a cholinesterase and lower the hydrolytic activity.

However, according to the method of Patent Reference 1, since the coloring reaction with the hydrolyzed product proceeds weakly and since the substrate degradation level is measured through absorptiometry, simple visual determination is impossible and the promptness of detection is problematic.

Based on the same principle as that of the method of Patent Reference 1, for example, AT-10/AT-25 (Agriscreen Ticket 10/25) is sold by NEOGEN as a detection kit for simple visual determination of the presence of organophosphate agrichemicals and carbamate agrichemicals in a sample.

Patent Reference 1: JP-A 09-107992

DISCLOSURE OF THE INVENTION

Problems that the Invention is to Solve

However, the above-mentioned detection kit is not always sufficient in point of the detection sensitivity thereof and, for example, its detection limit is around 7.0 ppm of carbaryl, 0.7 ppm of chlorpyrifos, 1.0 ppm of chlorpyrifos-methyl, and 2.0 ppm of diazinone.

Regarding the residual agrichemical analysis for cholinesterase-inhibiting organophosphate and carbamate agrichemicals, the Food Sanitation Act was partly revised in Japan on May 29, 2006, in which the Maximum Residue Limits (MRLs) of the residual agrichemical concentration in foods was changed; and as a result, almost all these kits are unsatisfactory in point of the sensitivity for the new MRLs, and improvement of the detection sensitivity is desired with keeping the simplicity of the kits.

The present invention has been made in consideration of the above-mentioned situation, and its object is to provide a device, a kit and a method for high-sensitivity, low-cost and visual detection of a cholinesterase-inhibiting substance.

Means for Solving the Problems

In order to solve the above-mentioned problems, the invention first provides a device for detecting a cholinesterase-inhibiting substance comprising: a basal layer at the bottom of a container; and a cholinesterase-containing reaction layer which is fixed on the basal layer. Second, the invention provides the device, wherein the reaction layer has pores formed therein; and third, the invention provides the device wherein the basal layer and the reaction layer comprise a hydrophilic photo-crosslinkable resin.

Fourth, the invention provides a kit for detecting a cholinesterase-inhibiting substance comprising: the device of any of claims 1 to 3; a syringe; a column chip fittable to the tip of the syringe and filled with column particles therein, and a substrate capable of coloring through reaction with a cholinesterase, and fifth, the invention provides the kit of the above-mentioned fourth wherein the substrate capable of coloring through reaction with a cholinesterase is indoxyl acetate.

Further sixth, the invention provides a method for determining the presence of a cholinesterase-inhibiting substance in a sample, which comprises 1) adding a sample to the device of any of the above-mentioned first to the third, 2) adding thereto a substrate capable of coloring through reaction with a cholinesterase, and 3) determining the presence of a cholinesterase-inhibiting substance in the sample in the case where no coloration has occurred; seventh, the invention provides the method of the above-mentioned sixth, wherein the sample is, after trapped in the column and processed for oxidation, added to the detection device of any of the above-mentioned first to the third; eighth, the invention provides a method for determining the presence of an organophosphate agrichemical in a sample, which comprises 1) trapping a sample in a column and processing it for oxidation, 2) adding the sample to the detection device of any of the above-mentioned first to the third, 3) adding thereto a substrate capable of coloring through reaction with a cholinesterase, and 4) determining the presence of a cholinesterase-inhibiting substance in the sample in the case where no coloration has occurred; and ninth, the invention provides the method of the above-mentioned sixth to the eighth, wherein the substrate capable of coloring through reaction with a cholinesterase is indoxyl acetate.

Advantage of the Invention

In the cholinesterase-inhibiting substance detection device of the invention, the amount of the liquid to be used for forming the reaction layer may be small owing to the presence of the basal layer therein, and the amount of the cholinesterase to be used in the reaction layer may be reduced, and the cost may be thereby reduced.

Further, since the reaction layer has pores, a solution sample can efficiently permeate thereinto, and therefore the presence or absence of cholinesterase inhibitory reaction can be detected rapidly and with high sensitivity.

In addition, when the cholinesterase-inhibiting substance detection kit of the invention is used, the detection method of the invention can be carried out with ease; and according to the detection method of the invention, since an organophosphate agrichemical can be changed to the oxon form thereof on the column, prior to analysis, the reaction can be streamlined and a high-concentration oxidizing agent can be used, and therefore, the detection sensitivity can be thereby increased. In addition, since the inspection result makes it possible to determine the presence of a cholinesterase-inhibiting substance in a simple manner through visual confirmation of the coloration of the reaction layer in the container, the invention enables easy inspection for residual agrichemicals at the shipping site or the sales site, therefore greatly contributing toward the safety of foods, drinkable water, etc.

[Description of Reference Numerals]

Figure 1:
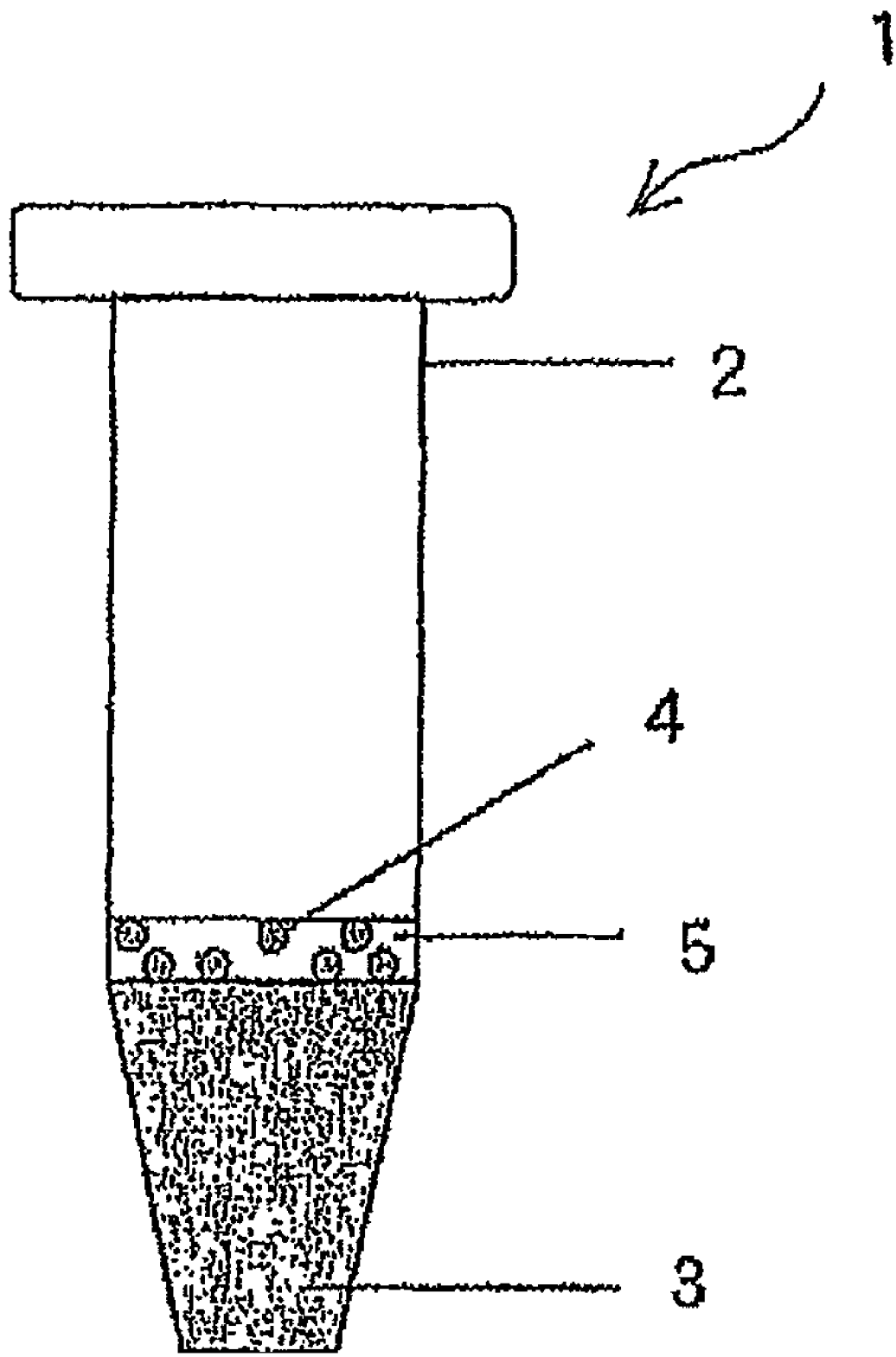
FIG. 1 is a schematic constitutional view of a cholinesterase-inhibiting substance detection device of the invention.

| | |
|---|---|
| 1. | Cholinesterase-inhibiting substance detection device |
| 2. | Container |
| 3. | Basal layer |
| 4. | Cholinesterase |
| 5. | Reaction layer |
| 6. | Syringe |
| 7. | Column chip |
| 8. | Column |
| 9. | Oxidizing agent |
| 10. | Eluate |

BEST MODE FOR CARRYING OUT THE INVENTION

The substance capable of being detected in the invention is a cholinesterase-inhibiting substance, and is one or more of organophosphate agrichemicals, carbamate agrichemicals, fluorine, arsenic, etc.

"Detection" as referred to herein means determination of the presence or absence of a specific substance in a sample.

A concrete example of the cholinesterase-inhibiting substance detection device of the invention is described with reference to FIG. 1.

In the detection device 1, a reaction layer 5 containing a cholinesterase 4 is, as stacked thereon, fixed on the basal layer 3 at the bottom inside the container 2; and a sample to be analyzed is added to the device, which enables visual determination of the presence or absence of cholinesterase inhibitory reaction in the reaction layer 5.

For the basal layer 3 and the reaction layer 5, preferred is a material not causing any damage on the enzymatic activity in fixation; and for example, the layers may be formed of a hydrophilic photo-crosslinkable resin. Concretely, first, a hydrophilic photo-crosslinkable resin is added to the container 2 and photo-crosslinked to form the basal layer 3 therein, and further a hydrophilic photo-crosslinkable resin containing a cholinesterase 4 is superposed on the top of the basal layer 3 and then photo-crosslinked to form the reaction layer 5 thereon.

The basal layer 3 is so designed that it serves as a base for physically stabilizing the bonding of the reaction layer 5 to the container 2 and enables to form the reaction layer as a thin layer, whereby the amount of the cholinesterase 4 to be contained in the reaction layer 5 can be reduced. The hydrophilic photo-crosslinkable resin for use for the basal layer 3 and the reaction layer 5 may be the same.

The reaction layer 5 contains a cholinesterase 4. As the cholinesterase 4, usable is any of acetylcholinesterase that reacts specifically with acetylcholine or butyrylcholinesterase that reacts with general choline ester; but in the invention, in particular, use of butyrylcholinesterase is a preferred embodiment.

In case where butyrylcholinesterase is used, one having the ability to intensely color in reaction with the cholinesterase and capable of forming a lipid-soluble product can be used for the coloring substrate; and for example, usable are indoxyl acetate, 5-bromo-6-chloro-3-indoxyl butyrate, 5-bromo-6-chloro-3-indoxyl caprylate, 5-bromo-4-chloro-3-indoxyl palmitate, etc.; and in consideration of the colorability and the like, preferred is indoxyl acetate.

For example, in case where indoxyl acetate is used, it forms indigo through hydrolysis with butyrylcholinesterase. Indigo has a maximum absorption wavelength at around 670 nm and colors in blue, and this is soluble in lipid, and therefore does not diffuse in the sample liquid but remains in the resin. Accordingly, in case where butyrylcholinesterase and indoxyl acetate are used, it is possible to evade the sensitivity depression owing to the reduction in the degree of coloration through diffusion, and in addition, any minor color change can be visually confirmed.

On the other hand, in case where acetylcholinesterase is used, 5,5'-dithiobis-2-nitrobenzoic acid (DTNB) can be used as the coloring substrate; in this case, however, 5-thio-2-nitrobenzoic acid (TNB) to be formed is soluble in water, and therefore diffuses in the sample solution from the resin. Further, TNB has a maximum absorption wavelength at around 412 nm and colors in yellow, and therefore it is difficult to visually confirm minor color change in the solution. Accordingly, in the invention, butyrylcholinesterase is preferably used.

Further, the reaction layer 5 is preferably so designed as to have a large number of pores through aeration treatment or stirring. The pores each run from the surface of the reaction layer to the cholinesterase inside the reaction layer, therefore enabling penetration of the sample solution not only in the surface of the reaction layer but also in the depth thereof, and accordingly, the contact between the cholinesterase 4 and the sample solution is further enhanced. Regarding the size thereof, the pores may be formed in accordance with the viscosity of the sample solution, preferably having a size of from 100 μm to 1000 μm, more preferably around 500 μm.

Accordingly, in case where a cholinesterase-inhibiting substance exists in a sample, cholinesterase inhibitory reaction can surely occur.

Further, the container 2 of the detection device 1 of the invention is preferably sealable and excellent in impact resistance and chemical resistance, for which, for example, usable is a plastic microtube; and more concretely, usable are commercial products such as Eppendols "Safelock Tube", etc. In consideration of the easiness in stirring a solution therein and the physical stability of the resin to be fixed at the bottom thereof, the size of the container is preferably 1.5 mL; and in consideration of stirring a liquid in the container, the capacity of the resin to be fixed therein is preferably 100 μL or so at the bottom and 30 μL or so in the reaction zone.

The detection kit of the invention comprises the above-mentioned detection device of the invention, a syringe, a column chip and a coloring substrate.

FIG. 2(a) is a schematic outline view showing a condition of bonding a syringe and a column chip to each other; and FIG. 2(b) is an enlarged schematic view of the column chip.

As shown in FIG. 2(a), the detection kit of the invention is used with a column chip 7 fitted to the tip of the syringe 6.

The syringe 6 may be a disposable one, and in consideration of the easy handlability thereof, the capacity of the syringe is preferably 10 ml or so.

The column chip 7 is filled with column particles 8 inside the tip thereof. In consideration of the sampling operability and the capability of sample concentration therein, preferred are those capable of dealing with a liquid in an amount as minor as possible therein; and commercial micropipette chips are usable. In consideration of the amount of the solution to be used therein, the size of the column chip is preferably 100 μL or so.

The column chip 7 of the type is fitted to the tip of the syringe 6, therefore enabling use of a large amount of a liquid therein, and the sample can be thereby concentrated in the column 8. In the detection kit of the invention, the column chip 7 may be previously connected to the syringe 6 to be a kit constituent.

The coloring substrate to be contained in the kit may be one that colors intensely through reaction with a cholinesterase and forms a lipid-soluble product, as described in the above; and for example, indoxyl acetate is preferably used. Hydrolysis with the butyrylcholinesterase in the reaction layer in the detection device of the invention forms lipid-soluble indigo and colors in blue in the resin, and this can be visually confirmed.

Figure 3:
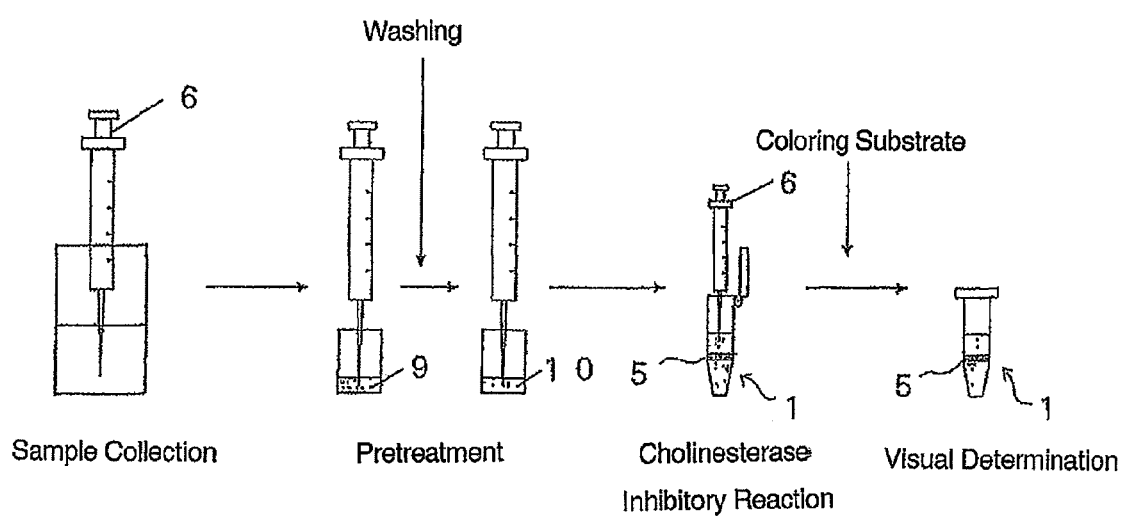
FIG. 3 is a process view showing a cholinesterase-inhibiting substance detection method.

Next described is a process of the detection method of the invention, with reference to FIG. 3.

In the detection method of the invention, drinkable water or the like may be a sample. In case of inspection of residual agrichemicals in agricultural crops or the like, for example, an agricultural crop is put into a bag or the like along with water thereinto, sealed up and strongly shaken to be a sample.

The sample is collected with a syringe 6 so as to make the sample absorbed by the column therein, and then this is processed through a process of 1) pretreatment of the sample, 2) addition of the sample to the detection device of the invention (for cholinesterase inhibitory reaction), and 3) addition of a coloring substrate thereto; and after the process, the presence or absence of a cholinesterase-inhibiting substance in the sample is visually determined.

The sample pretreatment is for increasing the detection sensitivity in case where the sample contains an organophosphate agrichemical.

Concretely, an oxidizing agent 9 is sucked by the syringe 6, and is brought into contact with the sample absorbed in the column, whereby the organophosphate agrichemical in the sample is converted into the oxon form thereof. As the oxidizing agent, for example, usable is N-bromosuccinimide (NBS), bromine water, hypochlorous acid, hydrogen peroxide or the like; and in consideration of the stability and the activation efficiency of the reagent, NBS is preferably used.

The pretreatment enhances the cholinesterase inhibitory ability by from 100 to 1000 times or so, and the detection sensitivity can be thereby increased.

The conversion into the oxon form can be attained by adding an oxidizing agent to the sample; however, in this case, the unreacted oxidizing agent may also be reacted with cholinesterase, and therefore in consideration of the oxidizing agent-caused deactivation of cholinesterase, only a low-concentration oxidizing agent could be used.

Therefore, in the embodiment of the invention where an oxidizing agent 9 is led to pass through the column in which a sample (organophosphate agrichemical) is absorbed, the sample can be treated with the oxidizing agent 9 having a high concentration and then the unreacted oxidizing agent 9 can be discarded. Accordingly, the conversion into the oxon form can be sufficient, and high-sensitivity detection is thereby possible.

Next, the pretreated sample is eluted from the column to give an eluate 10. The sample elution may be attained according to a known method. The eluate 10 is added to the detection device 1 of the invention. In case where the sample contains a cholinesterase-inhibiting substance, cholinesterase inhibitory reaction may occur in the reaction layer 5 in the detection device 1.

Subsequently, a coloring substrate is added to the detection device. In this, as the method of detecting the inhibitory reaction, an embodiment may also be employed where a substrate capable of reacting with a cholinesterase is added to the device and a coloring agent for detecting the product of the reaction is added thereto.

In case where the sample contains a cholinesterase-inhibiting substance, there does not occur hydrolysis of the coloring substance with the cholinesterase, and therefore the reaction layer 5 is kept colorless and transparent as such.

On the other hand, in case where the sample does not contain a cholinesterase-inhibiting substance, the reaction layer 5 colors through hydrolysis of the coloring substance therein. In case where indoxyl acetate is used as the coloring substrate, blue coloration can be visually confirmed.

As described in the above, according to the invention, the presence or absence of a cholinesterase-inhibiting substance in a sample can be determined in a simple manner with high sensitivity; and in particular, an organophosphate agrichemical in a sample may be pretreated in the manner as above and a cholinesterase-inhibiting substance therein can be detected with high sensitivity.

EXAMPLES

Example 1

Detection of Organophosphate Agrichemical

According to the process shown in FIG. 3, an organophosphate agrichemical was detected.

Figure 2:
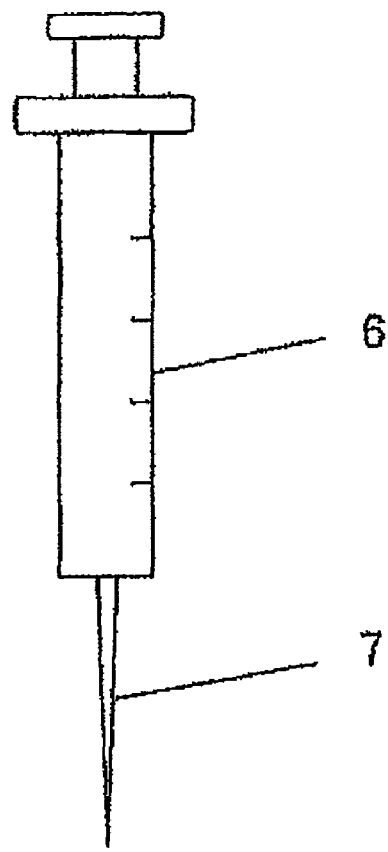
FIG. 2 is a schematic view showing a syringe and a column chip for use for concentration of a sample and for oxidation of an organophosphate agrichemical.
Figure 2:
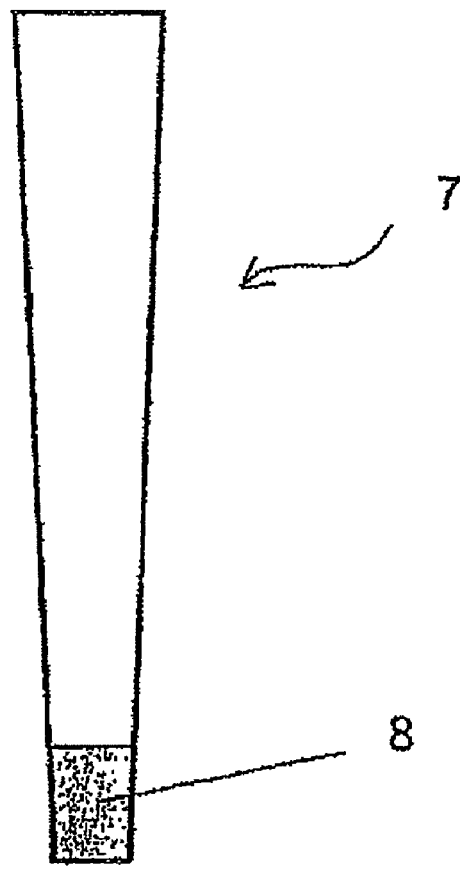

First prepared was 10 mL of an aqueous solution of a diazinone standard liquid of an organophosphate agrichemical having a diluted concentration of 0.1 ppb as a sample; and this was sucked in the syringe with a column chip connected to the tip thereof, as shown in FIG. 2.

The sucked solution was discharged in a beaker and again sucked, and this cycle was repeated three times whereby the sample diazinone was adsorbed by the column. Subsequently, in the same manner, 1 mL of 1% NBS solution was sucked and discharged and was thus converted into the oxon form thereof, and then diazinone was eluted from the column.

The eluate was added to the detection device shown in FIG. 1 and inhibited cholinesterase reaction therein. After 5 minutes, a coloring substrate of an indoxyl acetate solution was added to the device, and is formed chromogen for 5 minutes. As a result, the enzymatic activity of the cholinesterase was inhibited by diazinone and coloration did not occur; and diazinone was detected at a concentration level of 0.1 ppb.

In case where the sample did not contain diazinone, it colored in blue, which confirmed sure detection of an organophosphate agrichemical according to the method of the invention.

Comparative Example 1

Effect of Oxidation Treatment

This is a comparative experiment for confirming the effect of oxidation treatment (NBS solution suction treatment) in Example 1. In the same manner as in Example 1, the column was made to adsorb diazinone in the sample, and then not processed for oxidation treatment (NBS solution suction treatment), diazinone was eluted from the column. The eluate was added to the detection device, and an indoxyl acetate solution was added to the device.

As a result, the detection level of diazinone lowered to 5 ppm (5000 ppb), which confirmed the effectiveness of oxidation treatment.

Example 2

Detection of Carbamate Agrichemical

The detection method was to follow the process shown in FIG. 3; however, since a carbamate agrichemical was the object to be detected, the NBS solution suction and discharge operation attained in Example 1 was omitted here.

As a sample, prepared was 10 mL of an aqueous solution of a carbaryl (NAC) standard liquid of a carbamate agrichemical having a diluted concentration of 10 ppb; and this was sucked in the syringe with a column chip connected to the tip thereof, as shown in FIG. 2.

The sucked solution was discharged in a beaker and again sucked, and this cycle was repeated three times whereby the sample NAC was adsorbed by the column. Subsequently, NAC was eluted from the column, and put into the device to undergo an enzyme inhibitory reaction for 5 minutes therein.

After 5 minutes, a coloring substrate of an indoxyl acetate solution was added to the device, and underwent coloration reaction for 5 minutes. As a result, the enzymatic activity of the cholinesterase was inhibited by NAC and coloration did not occur; and NAC was detected at a concentration level of 10 ppb.

Example 3

Other agrichemical substances were tested in the same manner as in Example 1 and Example 2, and the following results were obtained.

TABLE 1

| Agrichemical | Detection Level (ppb) | Agrichemical | Detection Level (ppb) |
| --- | --- | --- | --- |
| EPN | 40 | terbufos | 10 |
| azinphos-ethyl | 1 | parathion | 0.8 |
| azinphos-methyl | 8 | pyridaphenthion | 1 |
| isoxathion | 0.2 | pyrimiphos-methyl | 20 |
| ethion | 10 | fenamiphos | 4 |
| etoprophos | 100 | fenitrothion | 40 |
| etorifos | 10 | fensulfothion | 100 |
| quinalphos | 0.1 | butamifos | 100 |
| coumafos | 2 | propafos | 1 |
| chlorpyrifos | 0.2 | bromofos-ethyl | 10 |
| chloropyrifos-methyl | 1 | phosalone | 6 |
| chlorfenvinphos | 40 | phorate | 80 |
| salithion | 100 | monocrotophos | 100 |
| cyanfenphos | 100 | thiodicarb* | 20 |
| dichlofenthion | 100 | pirimicarb* | 8 |
| dimethylvinphos(E) | 100 | | |
| dimethylvinphos(Z) | 100 | | |
| sulprofos | 20 | | |

As shown in Table 1, it has been confirmed that the device and the method of the invention are more excellent in the detection sensitivity than conventional methods. The detection values shown in Examples 1, 2 and Table 1 above may vary depending on the coloring substance, the column and others, and do not mean the detection limit in the device and the method of the invention

INDUSTRIAL APPLICABILITY

Provided are a device, a kit and a method for high-sensitivity detection of a cholinesterase-inhibiting substance through visual determination at low cost.

The invention claimed is:

1. A device for detecting a cholinesterase-inhibiting substance, comprising:
    a basal layer fixed at the bottom of a container, and
    a cholinesterase-containing reaction layer which is fixed on an upper surface of the basal layer,
wherein the basal layer is formed by photo-crosslinking a hydrophilic photo-crosslinkable resin being added into a bottom of the container, and the cholinesterase-containing reaction layer is formed by photo-crosslinking a cholinesterase-containing hydrophilic photo-crosslinkable resin being superposed on the basal layer.

2. The device as claimed in claim 1, wherein the reaction layer has pores formed therein, and the pores have a size of 100 μm to 1000 μm.

3. The device as claimed in claim 1, wherein the container is a plastic microtube.

* * * * *